United States Patent [19]
Dobbs

[11] Patent Number: 5,668,851
[45] Date of Patent: Sep. 16, 1997

[54] X-RAY TOMOGRAPHY SYSTEM WITH STABILIZED DETECTOR RESPONSE

[75] Inventor: John Dobbs, Hamilton, Mass.

[73] Assignee: Analogic Corporation, Peabody, Mass.

[21] Appl. No.: 668,538

[22] Filed: Jun. 21, 1996

[51] Int. Cl.⁶ .................................................. A61B 6/03
[52] U.S. Cl. ............................... 378/19; 378/7; 378/154
[58] Field of Search .............................. 378/4, 7, 19, 154, 378/155

[56] References Cited

U.S. PATENT DOCUMENTS

| | | | |
|---|---|---|---|
| 4,338,521 | 7/1982 | Shaw et al. | 250/370.11 |
| 4,866,744 | 9/1989 | Yoshida | 378/7 |
| 4,987,591 | 1/1991 | Bernardi | 378/19 |
| 5,025,462 | 6/1991 | Saito et al. | 378/19 |
| 5,487,098 | 1/1996 | Dobbs et al. | 378/19 |

Primary Examiner—David P. Porta
Assistant Examiner—David Vernon Bruce
Attorney, Agent, or Firm—Lappin & Kusmer LLP

[57] ABSTRACT

In a CT scanning system having an x-ray source, a plurality of x-ray detector modules, and a plurality of anti-scatter plate modules, signal instability and the associated introduction of artifacts into the reconstructed images are prevented by an alignment assembly which permits the anti-scatter plates to be substantially aligned with regions of substantially constant maximum sensitivity of corresponding detectors. Shadows cast by the anti-scatter plates fall entirely within these regions of substantially constant maximum sensitivity to radiation, thereby minimizing signal modulation due to thermal effects or relative movement of the source, the detectors and the anti-scatter plates between scans.

10 Claims, 7 Drawing Sheets

X-RAY TOMOGRAPHY SYSTEM WITH STABILIZED DETECTOR RESPONSE

FIELD OF THE INVENTION

This invention relates generally to x-ray computed tomography (CT) systems, and more particularly to arrangements for x-ray detector assemblies and anti-scatter plate assemblies within such systems.

BACKGROUND OF THE INVENTION

Third-generation CT scanners typically include an x-ray source and an array of x-ray detectors secured respectively on diametrically opposite sides of an annular disk, the latter being rotatably mounted within a gantry support. During a scan of a patient located within the opening of the disk, the disk rotates about a rotation axis while x-rays pass from the focal spot of the X-ray source through the patient to the detector system.

The x-ray source and detector array are positioned so that the x-ray paths between the focal spot and each detector all lie in the same plane (the so-called "slice plane", "rotation plane" or "scanning plane") which is normal to the rotation axis of the disk. Because the ray paths originate from substantially a point source and extend at different angles to the detectors, the ray paths resemble a fan, and thus the term "fan beam" is used to describe all of the ray paths at any one instant of time. The radiation that is detected by a single detector at a measuring interval of time during a scan is considered a "ray". The ray is partially attenuated by the mass of the patient in its path and each detector generates a single intensity measurement as a function of the attenuation, and thus of the density of the portion of the patient in the path of the ray from the focal spot to that detector. These x-ray intensity measurements, or projections, are typically performed during prescribed measurement intervals at each of a plurality of angular disk positions.

Ideally, all of the radiation within the fan beam should be of uniform intensity during the scan, and all of the detectors should have a uniform input-output response (or transfer function), i.e., all of the detectors ideally should provide the same output signal for a given input signal level of X-radiation. In addition, ideally there should be no variation in the stability of the response of the detector system to the radiation, i.e., the signals produced from the detector system should not drift between successive or periodic scans.

Various types of detectors have been developed, including gas and solid state types. A typical solid state detector includes a scintillating crystal which converts high energy x-radiation photons into low energy visible light photons, and a photodiode which converts the low energy visible light photons into extremely low-amplitude electrical currents (i.e., on the order of picoamperes to nanoamperes). The extremely low-amplitude current output of each detector represents the x-ray flux incident on the detector. The outputs of the detector array are transmitted via an array of conductors to a data acquisition system (DAS) for signal processing.

Because resolution of the resulting image is a function of the size of the detectors, a CT scanner system typically includes hundreds of detectors which are extremely closely spaced within the fan beam arc. For reducing the costs of such detector arrays, preassembled solid state detector modules, each comprising several solid state detectors, have been described in U.S. Pat. No. 5,487,098 issued to John Dobbs and David Banks, and assigned to the present assignee (hereinafter, "the '098 Patent"), and incorporated by reference into this application. For example, one third-generation CT scanner system manufactured by the present assignee includes 384 detectors provided by 24 modules of 16 detectors each and closely spaced within an arc which subtends not more than 48 degrees. The width of a single detector is thus on the order of a millimeter.

Each detector module is typically enclosed on all sides in an electrically conductive, optically opaque shield which is substantially transparent to x-rays. The shield around the module is typically formed from a thin reflective foil. In addition, each individual detector (hereinafter, "detector" or "detector crystal") within a module is surrounded by a white, highly reflective material which is on the order of at least 0.2 millimeter thick and which permits passage of x-rays, yet prevents excessive light leakage between the crystals. X-rays are thus able to impinge on the detector crystal from any angle; however, visible light generated in the crystal in response those x-rays is unable to pass, or reflect, from one detector to another because of the optically opaque shield around the detector, thus substantially reducing or eliminating cross-talk between adjacent detector channels.

Because of the coating thickness between adjacent detector crystals and the mechanical tolerances associated with the manufacture of the individual crystals, it is impractical to position the crystals sufficiently close to one another to achieve a truly continuous detecting region. Even the most closely spaced detector crystals in an array are separated by a distance of at least about 0.2 mm to accommodate the multiple layers of reflective material between them. This small spacing, or gap, between individual detector crystals is manifested as a region of diminished signal information in each projection of the patient. The existence of such regions diminishes the effectiveness with which the detector crystals can uniformly detect the radiation across the fan beam, and thus influences the accuracy and the resolution of the reconstructed image.

This condition is aggravated by the necessity to collimate the radiation prior to its impingement on the detector crystals. Because dense matter tends to scatter x-rays, it is necessary to preclude, to the greatest extent possible, the impingement upon the detector crystals of any radiation that does not traverse a straight path from the focal spot of the x-ray source to each detector crystal. To preclude the impingement of such stray or scattered radiation on the detector crystals, an array of elongated, thin collimation, or "anti-scatter", plates is positioned between the x-ray source and the detector crystals. The anti-scatter plates are opaque to X-rays and are aligned relative to the detector crystals so as to collimate, and thus permit passage of, substantially only those rays traversing a straight line from the source to a detector crystal. The anti-scatter plates are generally placed so that they are aligned with radial lines extending from the focal spot and corresponding gaps between adjacent detector crystals of the array so that they block any rays that impinge on the detector crystal at an angle which varies, for example, by no more than about three degrees from a normally incident ray along the respective ray path. The alignment of each anti-scatter plate with a corresponding gap between detectors insures that each anti-scatter plate shadows the least sensitive part of adjacent detectors, and thus a maximum amount of radiation is detected by the corresponding detector crystals. An advantageous anti-scatter plate alignment system is also described in the '098 patent.

In existing CT scanner systems, it is assumed that at least some spacing between each detector crystal in an array is necessary to accommodate the anti-scatter plates and the shadows they cast on the detector crystals. While each anti-scatter plate is extremely thin, e.g., on the order of 0.1 mm thick, it still occasionally blocks x-rays or creates a "shadow" on one or both of the corresponding adjacent detector crystals. A detector crystal which is "shadowed" by an anti-scatter plate generates a signal which is correspondingly reduced in strength relative to a signal from an unshadowed detector crystal. However, detector system response is affected much more by signal instability than by reduced signal strength. When the disk carrying the detector crystals and anti-scatter plates rotates during a scan, the anti-scatter plates can move over time as a result of thermal effects or of the rotation of the disk. This movement over time of the anti-scatter plates relative to the detector crystals produces variations in the extent of shadowing by an anti-scatter plate on a corresponding detector crystal. The result of this variable shadowing is that the output signal of a shadowed detector may be modulated by the moving anti-scatter plate. Even though the motion of the anti-scatter plates is slight in terms of spatial movement, because the output of each detector crystal is calibrated to an extremely precise degree (0.03%) and is used to make measurements at this level of precision, the amount of fluctuation in the current amplitude can be significant. Thus, prior to the present invention, it was believed that each anti-scatter plate should be as thin as possible and aligned as closely as possible with the corresponding gap between two adjacent detector crystals (the least sensitive part of each detector crystal) so as to minimize the casting of shadows on the detecting regions of the adjacent detector crystals, and thus minimize the modulation of the output signal from the detectors.

However, the optimum system design requires tradeoffs in the design of the detector assembly. On the one hand, it is desirable to make the gap between detector crystals as small as possible in order to more closely simulate a continuous detecting region. On the other hand, it is desirable to make the gap between adjacent detector crystals large enough to accommodate shadows from the anti-scatter plates and thus minimize the effects of the shadows cast by the plates on the detecting regions. This design tradeoff makes it highly impractical to locate the anti-scatter plates so that their shadows fall entirely within the gaps between the detector crystals and not on the detecting regions of the detector crystals. The sensitivity of a detector crystal to radiation is generally at a constant maximum value over the central detecting region of the detector crystal and falls off sharply near the edges of the crystal. Shadowing of the edge, and therefore a less sensitive region, of a detector crystal, i.e., near the gap between adjacent detector crystals, will still cause significant changes in signal intensity for relatively small movements of the anti-scatter plate, thus producing undesirable signal modulation and instability.

As a result of these conditions, extremely painstaking and accurate placement of the detector modules and the anti-scatter plates relative to one another has been required. To minimize shadowing, maximize the amount of direct radiation that is detected, minimize the detection of stray radiation, and prevent signal instability, virtually all relative movement between the plates and the detector crystals must be minimized or prevented. As the resolution of the detector crystals becomes greater, the crystals and the gaps between them become smaller, and the ability to keep the anti-scatter plate shadows entirely within the gap regions becomes increasingly impractical to achieve and maintain. Further, because the detecting region is not continuous but is instead an array of discrete detecting regions of substantially constant maximum sensitivity separated by regions of decreased sensitivity at the edges of a detector crystal, a small but potentially significant portion of the total radiation passing through the patient may not be detected. The resulting signals from the detectors are likely to be relatively unstable, and the images reconstructed from those signals may be distorted and obscured by artifacts introduced thereby.

It would therefore be an advantage in the art of CT scanner systems to overcome the disadvantages of the present systems.

OBJECTS OF THE INVENTION

It is therefore an object of the present invention to provide a CT scanner system having an anti-scatter plate assembly which can be precisely located relative to the x-ray source and the detector assembly in order to control the occurrence and location of shadows from the anti-scatter plates on the detector crystals.

It is another object of the invention to provide a CT scanner system having a detector assembly that does not require a minimum spacing between the detector crystals in order to accommodate anti-scatter plates.

It is another object of the invention to provide a CT scanner system which permits an anti-scatter plate assembly to be positioned so any shadows created by the presence of the anti-scatter plates in the radiation path and any movement of the plates relative to the detectors as a result of thermal effects or the rotation of the disk do not materially affect the signals generated by the detectors.

SUMMARY OF THE INVENTION

An x-ray scanning system according to the invention includes (a) a gantry including a disk for supporting an x-ray source and an x-ray detector assembly, and a frame for rotatably supporting the disk for rotation about a rotation axis, (b) an x-ray detector assembly including a plurality of x-ray detectors cooperative with the x-ray source, (c) an anti-scatter plate assembly having a plurality of anti-scatter plates disposed in the radiation path between the source and the detector assembly, and (d) a support structure connected to the disk for supporting the detector assembly and anti-scatter plate assembly. The scanning system further comprises an assembly for stabilizing the signals against modulation due to relative movement of the x-ray source, the detectors and the anti-scatter plates.

The signal stabilizing assembly comprises a positioning assembly for positioning the anti-scatter plate assembly relative to the detector assembly on the support structure so that each of the anti-scatter plates is substantially aligned with the continuous region of substantially constant maximum sensitivity to radiation of a corresponding detector. The result of this alignment of anti-scatter plates relative to the detectors is that all of the signals generated by the detectors are uniformly attenuated, so that any movement of the X-ray source or anti-scatter plate relative to the detector will still result in the anti-scatter plate shadowing the region of constant maximum sensitivity of a corresponding detector, so that the output of the detector will be unaffected by any movement of the anti-scatter plate. The impact on the signals of any relative movement of the source, plates and detectors due to thermal effects or rotation of the disk thus becomes negligible.

Each detector assembly and each anti-scatter plate assembly preferably is a modular unit having a respective reference surface for mating with the reference surface of the support structure. The support structure preferably includes a positioning assembly extending from the base reference surface and fixed relative to the support structure. When the anti-scatter plate module is positioned on the support structure relative to the detector module, the anti-scatter plates are substantially aligned with regions of substantially constant maximum sensitivity of corresponding detectors.

In one embodiment, the number of anti-scatter plates equals the number of detectors. In alternative embodiments, the number of anti-scatter plates need not equal the number of detectors and can be either greater or fewer than the number of detectors.

According to still another aspect of the invention, there is provided a method of stabilizing the signals generated by the detectors against modulation due to relative movement of the detector assembly, the x-ray source and the anti-scatter plate assembly in an x-ray system. According to the method, the anti-scatter plate assembly is positioned relative to the detector assembly so that the anti-scatter plates are substantially aligned with regions of substantially constant maximum sensitivity of corresponding detectors.

According to yet another aspect of the invention, there is provided an improvement in a modular arrangement for an x-ray detector assembly for use with a source of x-rays in an x-ray system. The arrangement includes at least one detector module having a reference surface and one or more detectors which are fixed relative to the reference surface for detecting x-rays generated by the source, and at least one anti-scatter plate module including a second reference surface and means fixed to the second reference surface for reducing the amount of scattered x-rays that are received by the detector. A base support assembly is secured to the x-ray system for supporting the detector and anti-scatter plate modules. The base support assembly has a base reference surface and a positioning assembly for properly positioning and fixing each of the modules to the base support assembly and relative to one another. The positioning assembly includes three pins extending through the base reference surface and fixed relative to the base support assembly such that the first pin cooperates with a detector module, the second pin cooperates with an anti-scatter plate module and the third pin cooperates with and is common to both the detector and anti-scatter plate modules so that the reference surfaces of each of the modules are in mutually confronting relationship with the base reference surface. The detector module and anti-scatter plate module are thus accurately positioned with respect to one another and to the source when the modules and base support assembly are secured to the x-ray system. The improvement comprises an assembly for stabilizing signals received from the detectors against modulation due to relative movement of the x-ray source, the detectors and the anti-scatter plates. In particular, this signal stabilizing assembly permits the anti-scatter plate modules and detector modules to be mounted relative to each other so that the anti-scatter plates are substantially aligned with the regions of constant maximum sensitivity of corresponding detectors.

Still other objects and advantages of the present invention will become readily apparent to those skilled in this art from the following detailed description wherein only two preferred embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative, and not restrictive, in nature.

BRIEF DESCRIPTION OF THE DRAWINGS

For a fuller understanding of the nature and objects of the present invention, reference should be had to the following detailed description taken in connection with the accompanying drawings, in which.

DETAILED DESCRIPTION OF THE DRAWINGS

Figure 1:
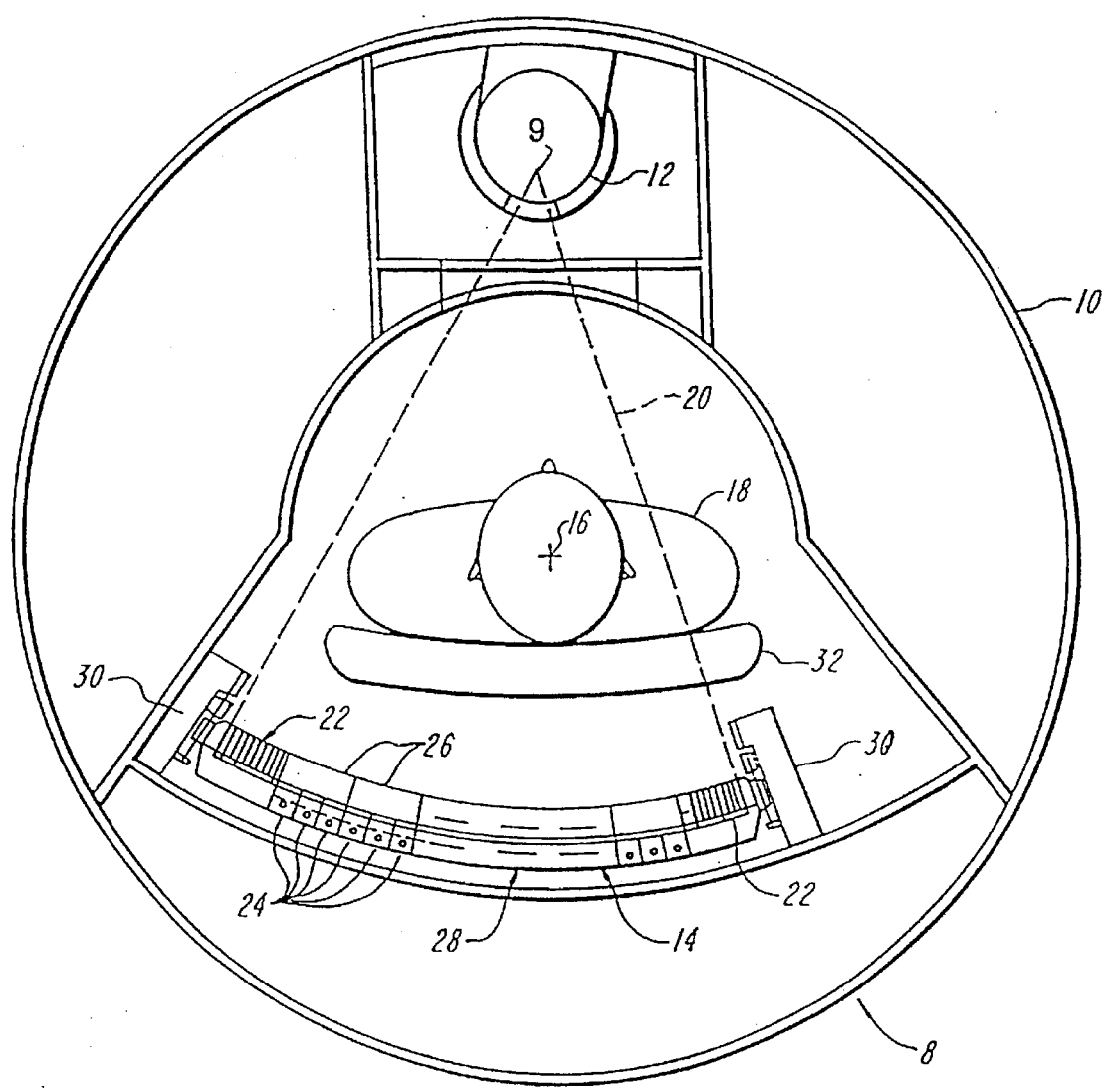
FIG. 1 is an axial view of a CT scanner system incorporating an embodiment of the present invention.

FIG. 1 represents a CT scanner system according to the present invention. To provide the data for a CT scan, scanner 8 includes a source 12 of X-rays and a detector assembly 14 mounted to a disk 10. Source 12 and detector assembly 14 are rotated about a rotation axis 16 (extending normal to the view shown in FIG. 1) so as to rotate around the object 18 that extends through the central opening of the disk during the CT scan. Object 18 may be a part of a live human patient, such as the head or torso. Source 12 emits within the scanning plane (normal to rotation axis 16) a continuous fan-shaped beam 20 of X-rays, which emanates from a focal spot 9 and extends to and is sensed by the detectors of assembly 14 after passing through object 18. An array of anti-scatter plates 22 is located between object 18 and the detectors of assembly 14 to substantially reduce the amount of scattered radiation sensed by the detectors.

In the preferred embodiment the detectors number 384 and cover an arc of 48°, although the number and angle can vary. Referring again to FIG. 1, disk 10, which may advantageously be of a lightweight material, such as aluminum, is caused to rotate rapidly and smoothly around axis 16. The disk 10 is of an open frame construction so that object 18 can be positioned through the opening of the disk. Object 18 may be supported, for example, on a pallet or table 32, which should be as transparent as practical to x-rays. As disk 10 rotates, detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image information. The image information may then be placed in memory, analyzed in a computer, or suitably displayed.

More specifically, referring again to FIG. 1, in accordance with the present invention the detector assembly 14 includes a base support element in the form of a supporting reference spine 28 provided with a flat datum or reference surface designed to be easily and precisely machined in the rectangular coordinate system of machine tools. The detectors and anti-scatter plates are each assembled into a plurality of identical modules 24 and 26, respectively, and the modules precisely machined also within the rectangular coordinates of standard machine tools. The modules are then accurately aligned and secured to the reference surface of the spine 28, and the spine supported by disk 10 with suitable supports, such as supports 30, so that the detectors all lie in the scanning plane and subtend an equal angle with respect to the focal spot 9 of the X-ray source 12.

Figure 2:
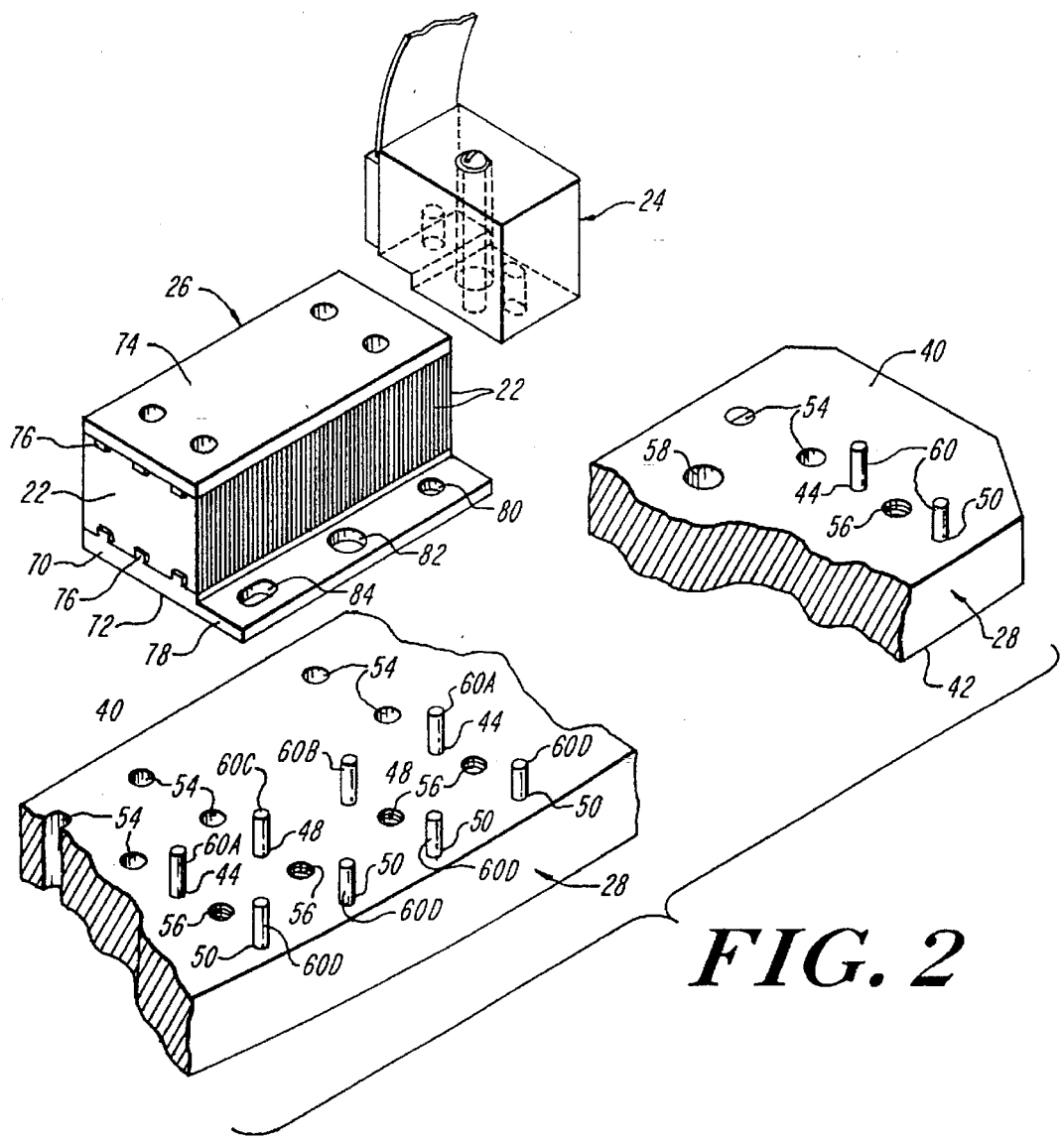
FIG. 2 is an exploded perspective view, partially cut away, illustrating the arrangement of a detector module and an anti-scatter plate module as mounted on a support structure.

Referring to FIG. 2, the detector assembly 14 comprises spine 28, detector modules 24 and anti-scatter plate modules 26. In use, the complete detector assembly is secured to disk 10 and may include, for example, one spine, eight anti-scatter plate modules and 24 detector modules with each detector module supporting 16 detectors. The spine 28 preferably is arc-shaped having a center of curvature coincident with the focal spot 9 of the source 12 when properly secured to disk 10. The spine also includes two flat parallel surfaces 40 and 42, of which surface 40 may be considered a front reference, or datum, surface. These flat surfaces allow the very accurate drilling of reference holes 44, 48, 50 and 56 and mounting holes 54, 58, into spine 28 from and normal to reference surface 40 using standard commercially available machine tools. Dowel pins 60A–D are fitted within the reference holes as detailed in the '098 patent.

For accurate positioning, anti-scatter plates 22 are first assembled into anti-scatter plate modules 26 which may include, for example, forty eight anti-scatter plates 22 mounted between a base plate 70 having a flat external reference surface 72 and a top plate 74, as shown in FIG. 2. The mutually opposing surfaces of base plate 70 and top plate 74 preferably include means for supporting the plates 22 so that each plate will be radially aligned with the focal spot 9 when the detector assembly is properly assembled and secured to the disk. The supporting means preferably are very thin raised ridges 76, provided with positioning slots for receiving the respective anti-scatter plates 22. The positioning slots are located on the raised ridges so that the anti-scatter plates 22 are aligned with the regions of constant maximum sensitivity of corresponding detectors when the respective anti-scatter plate and detector modules are mounted on the spine. This is accomplished in the present invention by locating the positioning slots uniformly either to the right or left from their locations as disclosed in the '098 patent by a distance equal to one-half the width of the detector crystal and of the gap between adjacent crystals. The construction of the anti-scatter plate module is further detailed in the '098 patent and is not further detailed herein.

Figure 3:
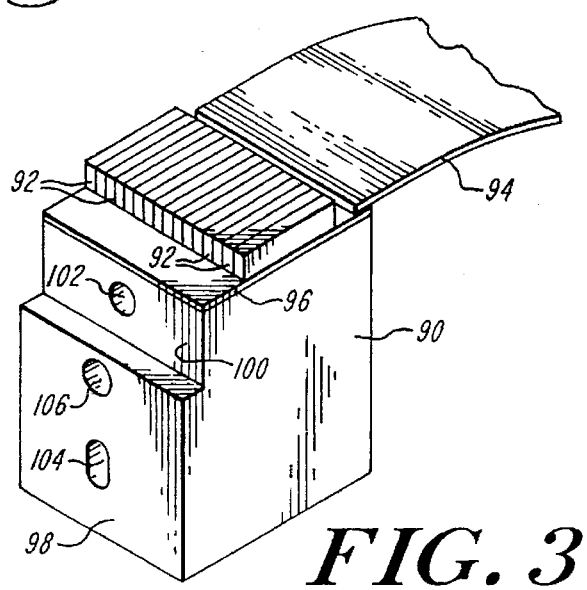
FIG. 3 is a perspective view of a detector module.

The preferred detector module 24 is shown in further detail in FIG. 3. This module comprises a metal block 90 with an array of solid state detectors 92 and a multi-conductor ribbon cable 94, or other flexible connection, mounted on one face thereof. Block 90 may also advantageously be of extruded aluminum, although other materials can be used. As shown in greater detail in FIGS. 4A–4B, the detectors 92 may each comprise a scintillating crystal 97 to convert x-ray energy into light, and a photodiode 99 to convert the light to electric current. The diodes may be formed by well known techniques on a substrate 96 and the crystals cemented directly on top of the diodes. Multi-conductor ribbon 94 may be attached by solder or otherwise to substrate 96 so that the output of each detector is individually fed through a corresponding conductor in the ribbon to the scanner signal processing components. The completed substrate assembly may be cemented onto block 90. Module 24 may contain, for example, 16 detectors, each having a width on the order of a millimeter. If they are mounted at ⅛ degree arc intervals, their centers will be less than two millimeters apart. Uniformity of detector spacing, as previously mentioned, is important for the assignment of measurements to the correct pixels in the reconstructed image. While uniformity of detector characteristics is desirable, in practice each detector is preferably calibrated over the range of anticipated temperatures. Good thermal bonding for uniform detector temperature therefore is desirable.

The positioning assembly comprises, for example, three pins or keys extending through the base reference surface and fixed relative to the support structure such that a first pin or key cooperates with a detector module, a second pin or key cooperates with an anti-scatter plate module, and a third pin or key cooperates with and is common to both modules so that the reference surfaces of the modules are in mutually confronting relationship with the base reference surface of the support structure. The detector modules and anti-scatter plate modules are thus accurately positioned relative to one another and to the source when the modules and support structure are secured to the x-ray system.

Each of the detector modules and anti-scatter plate modules includes one circular hole for tightly receiving the third of the three pins, as well as a slot having a width narrower than its length and being aligned with the hole. The width of the slot is adapted to tightly receive the respective first and second pins, while the length of the slot accommodates the tolerances between the first and third pins and between the second and third pins.

Further details of the detector assembly, the anti-scatter plate assembly, the arrangement of the detector modules and anti-scatter plate modules on the spine, and the means for adjusting them, are disclosed in the '098 patent and are not further described herein.

Figure 4:
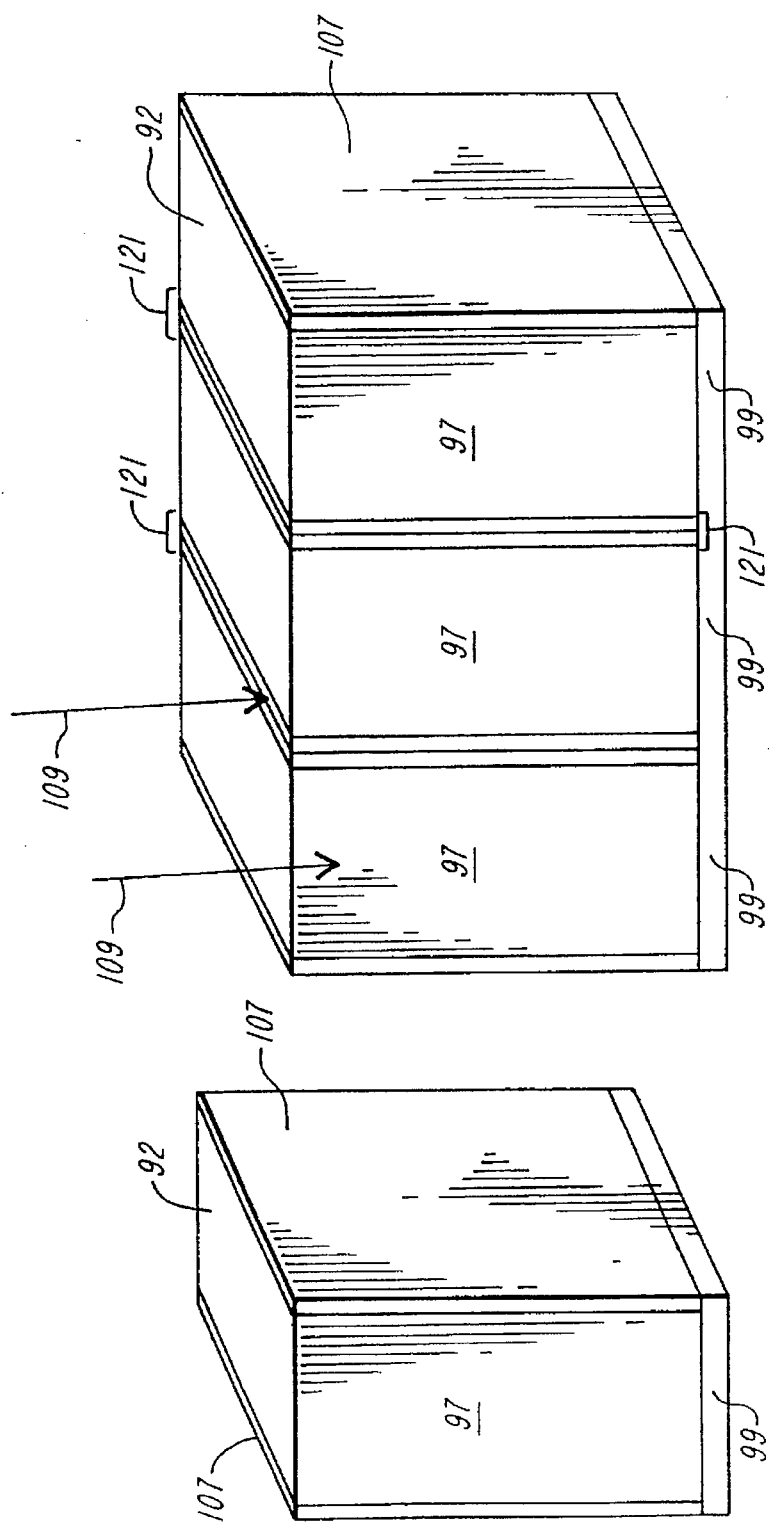
FIGS. 4A–B are simplified perspective views of single and multiple detectors, respectively, in an array.

As shown in greater detail in FIGS. 4A and 4B, each detector 92 is coated at least on mutually confronting sides (and preferably on all sides except the bottom which contacts the photodiode) with shielding made, for example, of a thin film 107 of highly optically reflective material in order to prevent leakage of light from one detector to another. However, this shielding around the detectors is transparent to x-rays (depicted as arrows 109). As previously stated, the region of the detector crystal between the foil coatings 107 is much more sensitive to x-radiation than the edges of the detector, in part because of the spacing or gap 121 created between adjacent detectors by the presence of fill 107. Although the detectors are quite closely spaced in a detector assembly, this small gap or spacing 121 between the detectors is typically on the order of approximately 0.2 mm. The signal intensity for radiation impinging substantially on the gap 121 between detector crystals is approximately 1% of the signal intensity for radiation impinging on the crystal.

Figure 5:
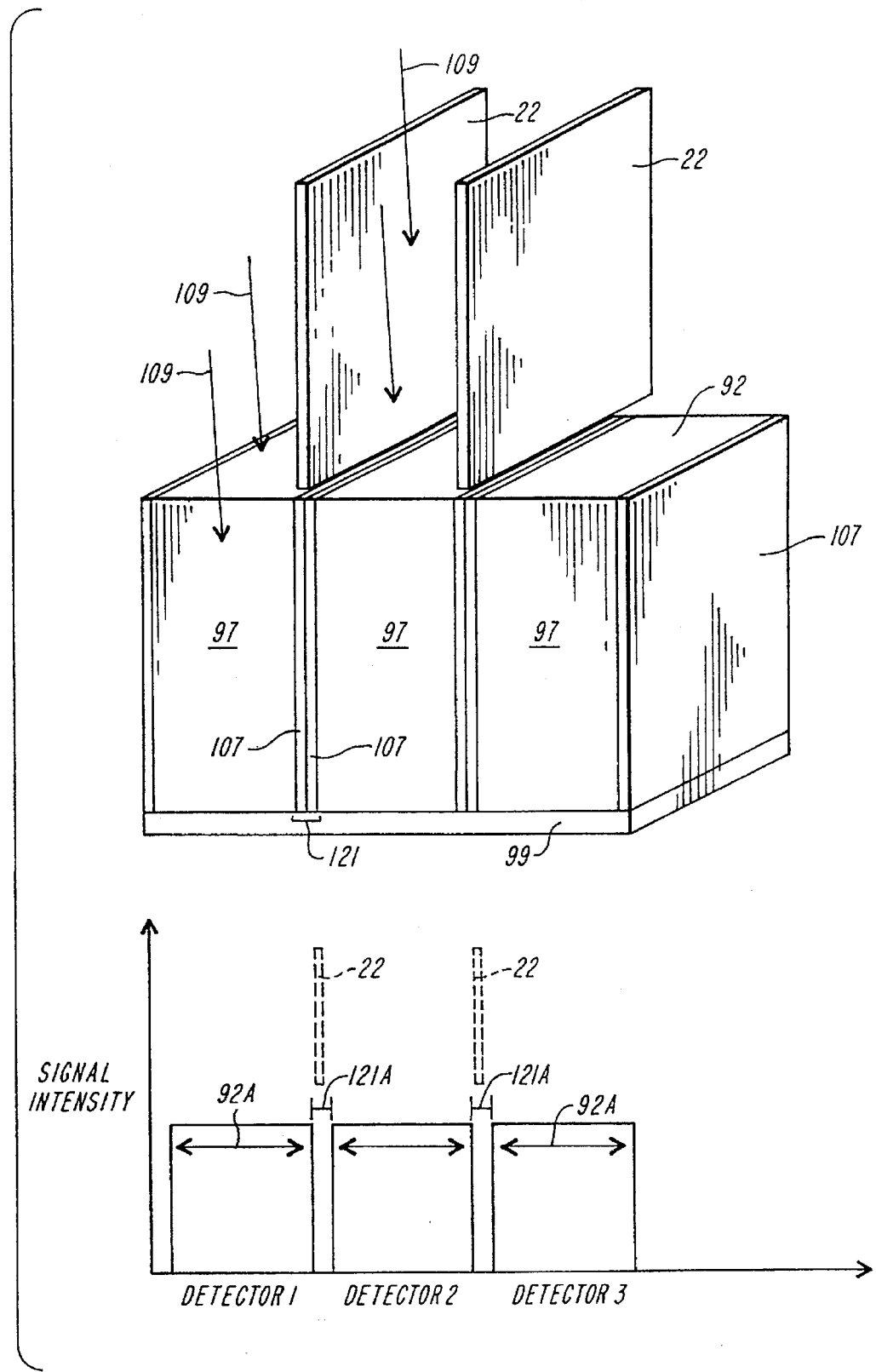
FIG. 5 is a simplified perspective view of a portion of a prior art x-ray system, showing the relative positions of detectors and anti-scatter plates, and a corresponding graph of the signal response of the detectors in a prior art x-ray system.

FIG. 5 illustrates in simplified form the relative positions of the detectors 92 and the anti-scatter plates 22 in a prior art x-ray system. In prior art CT systems the anti-scatter plates 22 are positioned so that they are substantially aligned with the gaps 121 (comprised of multiple layers of highly optically reflective material 107) between adjacent detectors. The placement of the anti-scatter plates over the gaps between the detectors in prior art x-ray systems was considered necessary to minimize the effect of plate shadowing on the detectors, thereby reducing modulation of the signals generated by the detectors due to relative movement of the anti-scatter plates. However, as can be appreciated by the corresponding graph of signal response below the detector diagram, it is extremely impractical and difficult to position the anti-scatter plates 22 precisely and entirely over the gap regions 121 between the detectors because of the extreme narrowness of the gap regions. The slightest relative movement of the x-ray source, the anti-scatter plates or the detectors can cause the anti-scatter plates 22 to become misaligned with respect to the gaps and to cast shadows over the detector crystals instead of over the gaps between the crystals. The intermittent introduction of a shadow onto the crystal introduces instability into the signals generated by that crystal and creates undesirable artifacts in the reconstructed image.

It is evident from FIG. 5 that placement of the anti-scatter plates 22 so that their shadows fall only over the gap regions 121 between the detectors would be desirable if the gap regions between the detectors were sufficiently large to accommodate them without causing shadows to impinge on the crystals. However, as the detectors are moved closer together, the gaps between them are reduced in size, and it becomes much more difficult to place the anti-scatter plates so that shadows occur only over the gap regions 121. As the gap regions of decreased sensitivity between the detectors become narrower, the anti-scatter plates must be placed with greater precision to overlie only those regions, and less relative movement between the anti-scatter plates and the detectors can be tolerated. Even if the anti-scatter plates were positioned precisely over an extremely narrow gap region 121 between detectors, any relatively small movements of the anti-scatter plates could cause their shadows to fall over the constant maximum sensitivity region of a detector, resulting in unpredictable changes in signal intensity as shadows flicker over both the regions of constant maximum sensitivity 92A and the less sensitive gap regions 121 between the detectors.

As can be seen in FIG. 5, the intensity of the signal from a detector which is not shadowed by an anti-scatter plate is a constant maximum value over the region of substantially constant sensitivity, corresponding to the regions 92A in the graph, and a very low level between the detectors, corresponding to regions 121A in the graph.

Figure 6:
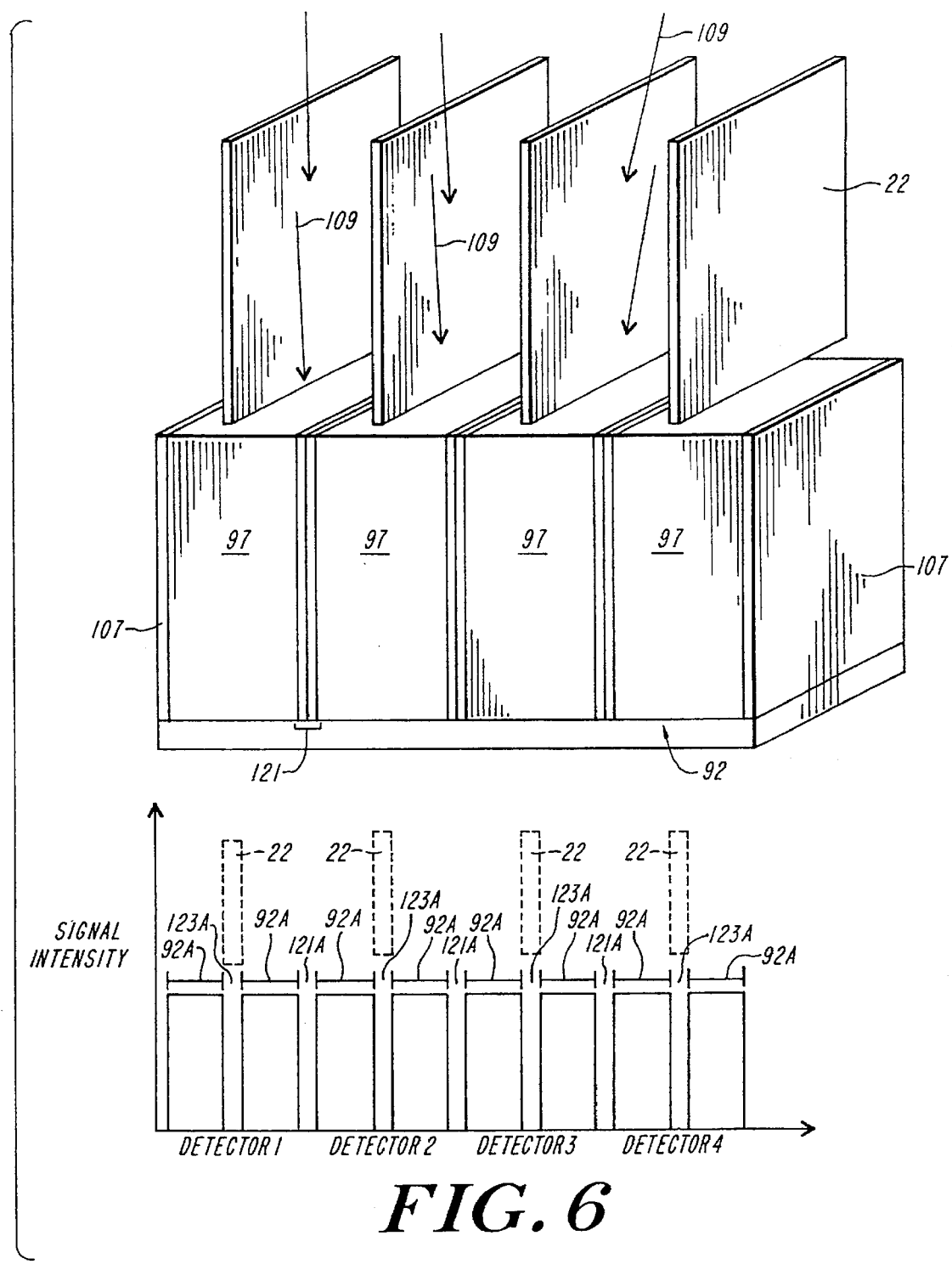
FIG. 6 is a simplified perspective view of a portion of an x-ray system according to the present invention, in which the anti-scatter plates are substantially aligned over regions of constant maximum sensitivity of corresponding detectors, and a corresponding graph of the signal response of the detectors in an x-ray system according to the present invention.

In contrast, FIG. 6 illustrates the relative positions of the anti-scatter plates and detectors of a preferred embodiment of an x-ray system according to the present invention. Note that the anti-scatter plates 22 are not positioned over the gap regions 121 between the detectors but are instead positioned to be substantially aligned with the regions of the detectors in which the sensitivity to radiation is at a maximum value which is substantially constant. As shown in FIG. 6, the intensity of a signal from a detector which is shadowed by an anti-scatter plate is at a maximum value over the region of constant maximum sensitivity, corresponding to regions 92A in the graph, and at a minimum value within the shadowed region directly beneath the anti-scatter plate, corresponding to regions 121A in the graph. Radiation which impinges on the detector crystals, corresponding to regions 92A, will generate signals of maximum intensity; radiation impinging on the gap region between detector crystals, corresponding to regions 121A, or on an anti-scatter plate, corresponding to regions 123A, will generate signals of minimum intensity. As previously mentioned, although the photodiodes underlying the detector crystals are relatively insensitive to radiation as compared to the sensitivity of a detector crystal, some radiation (on the order of 1%) is still detected in the gap region.

When the anti-scatter plates are positioned so that their shadows overlie the regions of constant maximum sensitivity of the detectors, as illustrated in FIG. 6, the intensity of the signals from each of the detectors is uniformly attenuated by the presence of the anti-scatter plates in the radiation path, but not otherwise affected by the location of the anti-scatter plates. Significantly, there are no abrupt discontinuities in the signal intensity (i. e., signal instability) as a result of shadows intermittently impinging on the regions of constant maximum sensitivity and regions of low sensitivity. A significant advantage of the present invention is that a minimum spacing between the detector crystals is no longer required to accommodate the anti-scatter plates, because the anti-scatter plates do not have to be positioned within the spaces between the detectors. As a result, the anti-scatter plates can be positioned to cast shadows anywhere over the relatively large detecting regions 92A instead of over the relatively narrow gap regions 121 between the detectors. Relative movement of the anti-scatter plates, detectors and x-ray source within this region can thus be tolerated to a significantly greater extent without adversely affecting the stability of the signals generated by the detectors.

This positioning of the anti-scatter plates over the regions of constant sensitivity of corresponding detectors instead of over the gap regions between detectors offers other significant advantages. First, the placement of anti-scatter plates so that they cast shadows over the central regions of the detectors, in which the sensitivity to high-energy photons is at a maximum value which is substantially uniform and constant, instead of over the less sensitive gap regions 121, causes the signals from the detectors to be uniformly attenuated (even when subjected to normal types of mechanical motion) and thus prevents signal modulation caused by thermal effects or intermittent shadowing of some or all of the detectors. Second, placement of the anti-scatter plates over the regions of constant sensitivity of the detectors instead of over the gap regions between the detectors permits a significantly greater extent of relative movement of the detectors, the anti-scatter plates and the x-ray source without adversely affecting the stability of the signals from the detectors. As discussed in connection with the prior art systems, the gap region 121A between the detectors, although relatively narrow, must nevertheless be sufficiently wide in order to accommodate the anti-scatter plates 22 therein. In contrast, the anti-scatter plates 22 in the embodiment of the present invention can be located anywhere within the regions of constant sensitivity 92A of the detectors and need not be placed in the gaps between the detectors. An important consequence of the present invention is that manufacturing tolerances of the detectors and the modular units housing them and the anti-scatter plates can be relaxed, as the precise locations of the anti-scatter plates relative to the detectors are no longer critical. For example, if the anti-scatter plates are placed over the gap regions between detectors, as in prior art systems, tolerances must be kept to within 0.0125 mm. In contrast, if the anti-scatter plates are placed over the regions of constant sensitivity of the detectors instead of over the gaps between the detectors, tolerances need only be within 0.1 mm, an order of magnitude greater than those required in the prior art systems.

According to a preferred embodiment of the invention, the anti-scatter plates 22 are aligned substantially over the regions of constant maximum sensitivity of corresponding detectors 92 by precisely locating the mounting slots for the anti-scatter plates 22 in the housing of the anti-scatter plate module 26. The desired alignment of the anti-scatter plates and detectors can be achieved in any way which accomplishes the desired objective, such as, for example, by simply bonding the anti-scatter plates in the desired locations within the anti-scatter plate module so that the relative positioning of the anti-scatter plates and detectors is as desired, or by precisely locating the reference holes and mounting holes on the spine, or by providing appropriately oriented slots instead of holes in the detector and/or anti-scatter plate modules for adjustable positioning of those modules on the spine relative to one another. Other means known in the art for establishing the desired alignment between the anti-scatter plates and the detectors are not detailed herein but are considered to be within the scope of the invention.

Figure 7A:
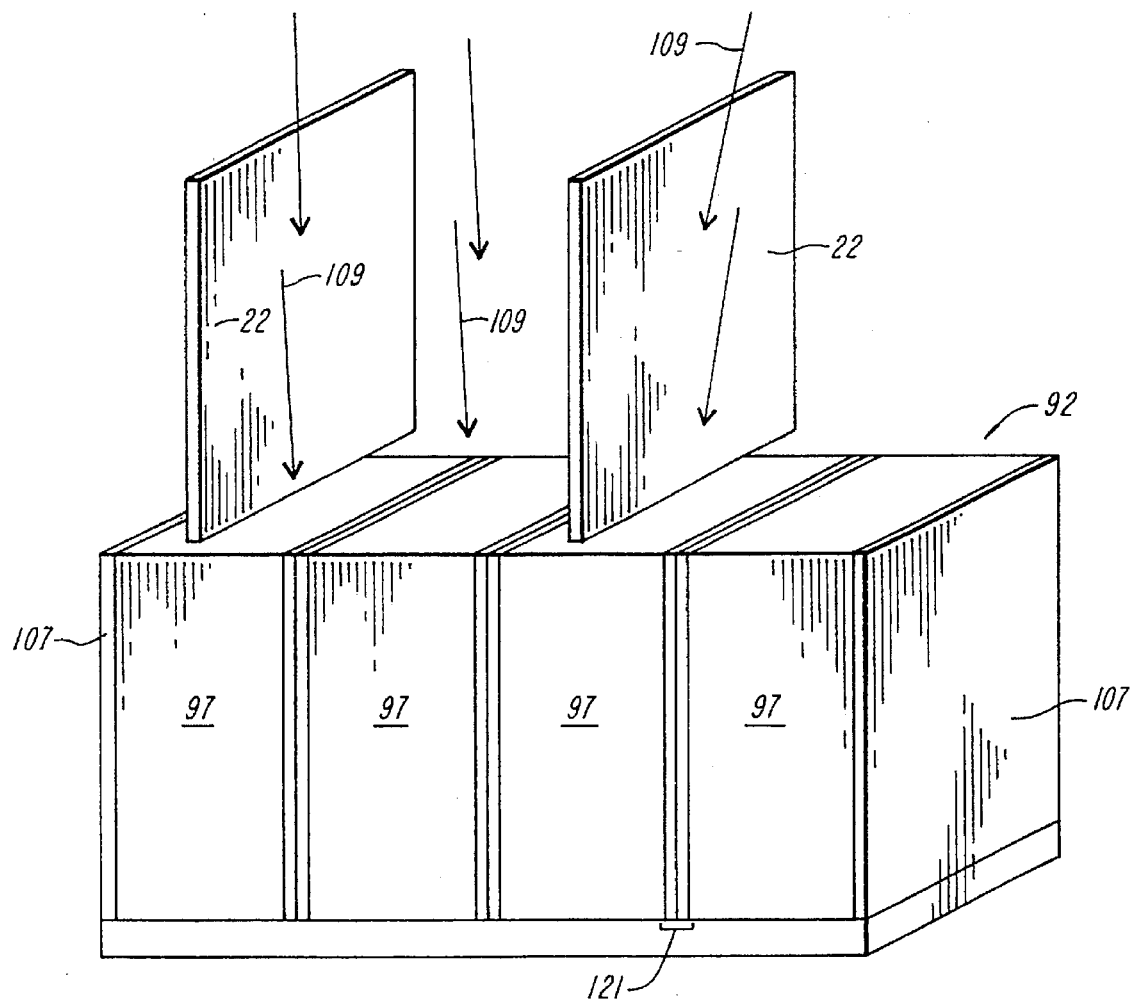
FIGS. 7A–B are simplified perspective views of a portion of an x-ray system according to two other embodiments of the present invention, respectively, in which the number of anti-scatter plates is not the same as the number of detector crystals.
Figure 7B:
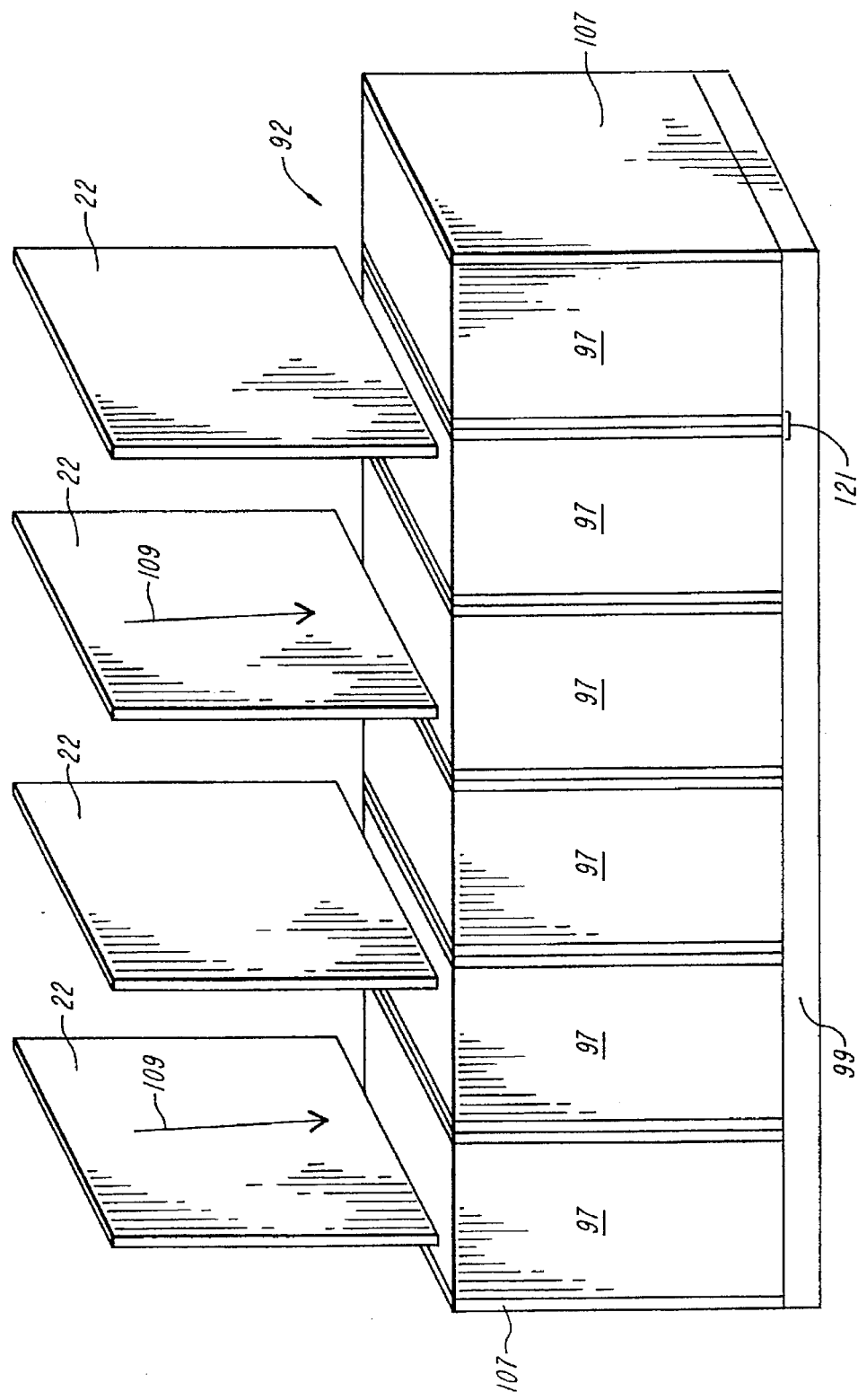

It should be noted that there need not be a one-to-one correspondence of anti-scatter plates to detectors. In certain applications it may be desirable to employ fewer anti-scatter plates than detectors, by increasing the distances between adjacent anti-scatter plates, as shown in FIGS. 7A–7B. Alternatively, it may be desirable to include more anti-scatter plates than the number of detectors. Accordingly, the system can include, for example, one anti-scatter plate for every n detectors, n being an integer or some fraction thereof, provided that the anti-scatter plates are not positioned over the gap regions between adjacent detectors. As shown in FIG. 7B, the anti-scatter plates 22 can be positioned anywhere relative to the corresponding detectors to cast shadows over the uniform detecting region of constant maximum sensitivity. Factors which influence the density of the anti-scatter plates relative to detectors include the physical dimensions of the anti-scatter plates, the extent of expected stray radiation, physical constraints, and the costs to manufacture and assemble the anti-scatter plate modules.

The desired alignment of the anti-scatter plates with the regions of constant maximum sensitivity of corresponding detectors can thus be accomplished easily and conveniently. As detector resolution increases, manufacturing tolerances will be tightened, and the detectors will have to be increasingly homogeneous in size. As a result, the gap regions between detectors can be expected to decrease in size, and it will become increasingly difficult and impractical to attempt to position and maintain the anti-scatter plates within the gaps between the detectors. Thus, it has become critically important to have an alternate scheme for placement of the anti-scatter plates which does not adversely impact the quality and accuracy of the reconstructed images.

The arrangement of the supports 30, and the ability of the spine to be adjusted in both the radial and tangential directions, are detailed in the '098 patent and are not considered a part of the present invention.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An x-ray scanning system of the type including (a) a gantry including a disk for supporting at least an x-ray source, and a frame for rotatably supporting the disk for rotation about a rotation axis, (b) an x-ray detector assembly including a plurality of x-ray detectors cooperative with said x-ray source, (c) an anti-scatter plate assembly having a plurality of anti-scatter plates disposed in the radiation path between said source and said detector assembly, and (d) a support structure connected to said disk for supporting said detector assembly and said anti-scatter plate assembly, said support structure having a base reference surface, said scanning system further comprising:

means for stabilizing said signals against modulation due to relative movement of said x-ray source, said detectors and said anti-scatter plates.

2. An x-ray scanning system according to claim 1, wherein said signal stabilizing means comprises means for positioning said anti-scatter plates relative to said x-ray detectors so that each of said anti-scatter plates is substantially aligned with a region of substantially constant maximum sensitivity of a corresponding detector.

3. An x-ray scanning system according to claim 2, wherein each detector assembly and each anti-scatter plate assembly is a modular unit having respective reference surfaces and wherein the support structure includes a positioning assembly extending from the base reference surface and fixed relative to the support structure for relative positioning of the detector modules and anti-scatter plate modules thereon.

4. An x-ray scanning system according to claim 3, wherein the number of anti-scatter plates is equal to the number of detectors.

5. An x-ray scanning system according to claim 3, wherein the number of anti-scatter plates is not equal to the number of detectors.

6. In an x-ray scanning system of the type including (a) a gantry including a disk for supporting at least an x-ray source, and a frame for rotatably supporting the disk for rotation about a rotation axis, (b) an x-ray detector assembly including a plurality of x-ray detectors cooperative with said x-ray source, (c) an anti-scatter plate assembly having a plurality of anti-scatter plates disposed in the radiation path between said source and said detector assembly, (d) a support structure connected to said disk for supporting said detector assembly and said anti-scatter plate assembly, and (e) a data acquisition system for processing signals received from said detectors, a method of stabilizing said signals against modulation due to relative movement of said x-ray source, said detector assembly, and said anti-scatter plate assembly, the method comprising the step of:

positioning said anti-scatter plate assembly relative to said detector assembly on said support structure so that said anti-scatter plates are substantially aligned with regions of substantially constant maximum sensitivity of corresponding detectors.

7. In a modular arrangement for an x-ray detector assembly for use with a source of x-rays in an x-ray system, the arrangement including at least one detector module having a reference surface and one or more detectors which are fixed relative to the reference surface for detecting x-rays generated by the source, at least one anti-scatter plate module including a second reference surface and means fixed to the second reference surface for reducing the amount of scattered x-rays that are received by the detector, base support means secured to the x-ray system for supporting the detector and anti-scatter plate modules and having a base reference surface and positioning means for properly positioning and fixing each of the modules to the base support means and relative to one another, the positioning means including three pins extending through the base reference surface and fixed relative to the base support means such that the first pin cooperates with a detector module, the second pin cooperates with an anti-scatter plate module and the third pin cooperates with and is common to both the detector and anti-scatter plate modules so that the reference surfaces of each of the modules are in mutually confronting relationship with the base reference surface and so that the detector module and anti-scatter module are accurately positioned with respect to one another and to the source when the modules and base support means are secured to the x-ray system, the improvement comprising:

means for stabilizing signals received from the detectors against modulation due to relative movement of said x-ray source, said detectors and said anti-scatter plates.

8. The arrangement of claim 7, wherein said signal stabilizing means comprises alignment means for aligning said anti-scatter modules relative to said detector modules so that said anti-scatter plates are substantially aligned with regions of substantially constant maximum sensitivity of corresponding detectors.

9. An x-ray scanning system according to claim 8, wherein the number of anti-scatter plates is equal to the number of detectors.

10. An x-ray scanning system according to claim 8, wherein the number of anti-scatter plates is not equal to the number of detectors.

* * * * *